(12) United States Patent
Yabiku

(10) Patent No.: US 7,361,917 B2
(45) Date of Patent: Apr. 22, 2008

(54) FAR-INFRARED GENERATOR FOR THERMOTHERAPY AND METHOD OF FAR-INFRARED IRRADIATION

(76) Inventor: Katsuko Yabiku, 226-4, Aza Kohatsu, Nishihara-cho, Nakagami-gun, Okinawa 903-0118 (JP)

( * ) Notice: Subject to any disclaimer, the term of this patent is extended or adjusted under 35 U.S.C. 154(b) by 0 days.

(21) Appl. No.: 10/546,918

(22) PCT Filed: Feb. 20, 2004

(86) PCT No.: PCT/JP2004/002024

§ 371 (c)(1), (2), (4) Date: Apr. 26, 2006

(87) PCT Pub. No.: WO2004/075986

PCT Pub. Date: Sep. 10, 2004

(65) Prior Publication Data

US 2006/0226378 A1 Oct. 12, 2006

(30) Foreign Application Priority Data

Feb. 26, 2003 (JP) ............................. 2003-050159

(51) Int. Cl.
*A61N 5/06* (2006.01)
(52) U.S. Cl. .................................. 250/504 R; 607/100
(58) Field of Classification Search ............ 250/504 R; 607/100
See application file for complete search history.

(56) References Cited

U.S. PATENT DOCUMENTS

| 2,582,617 | A | * | 1/1952 | August | ....................... 601/18 |
|---|---|---|---|---|---|
| 3,736,920 | A | * | 6/1973 | Mathers et al. | ................ 601/52 |
| D294,864 | S | * | 3/1988 | Gialanella | ................... D24/206 |
| 6,317,636 | B1 | * | 11/2001 | Fujii | ........................... 607/100 |
| 2004/0042965 | A1 | * | 3/2004 | Usui et al. | ..................... 424/40 |

FOREIGN PATENT DOCUMENTS

| JP | 63-18156 Y2 | 5/1988 |
|---|---|---|
| JP | 2-141445 U | 11/1990 |
| JP | 141445/1990 A | 11/1990 |
| JP | 3-25800 Y2 | 6/1991 |
| JP | 7-303709 A | 11/1995 |
| JP | 8-112302 A | 5/1996 |
| JP | 11-70175 A | 3/1999 |
| JP | 2000-140135 A | 5/2000 |
| JP | 2000-308668 A | 11/2000 |

* cited by examiner

*Primary Examiner*—Robert Kim
*Assistant Examiner*—Michael Maskell
(74) *Attorney, Agent, or Firm*—Birch, Stewart, Kolasch & Birch, LLP

(57) ABSTRACT

The present invention relates to a far-infrared ray generator, which is suitable for warming a human body partially or as a whole, and an object of the present invention is to effectively warm a deep part of a human body even at relatively low temperature by the far-infrared ray generator having high efficiency of generating far-infrared rays. In the present invention, far-infrared ray means, which generates far-infrared rays upon being heated by a heating element and which is used in a thermotherapy apparatus, includes a far-infrared ray generating member comprising only a radon generating rare element mineral or at least two of a tourmaline mineral, carbon and a radon generating rare element mineral so as to attain effective reaching of far-infrared rays to the deep part of the human body and warming said part. The far-infrared ray generating member may be applied to, for example, trowel-shaped, vibration-type and dome-shaped thermotherapy apparatuses.

3 Claims, 10 Drawing Sheets

FAR-INFRARED GENERATOR FOR THERMOTHERAPY AND METHOD OF FAR-INFRARED IRRADIATION

RELATED APPLICATIONS

This application is the U.S. national phase application of PCT Application PCT/JP2004/002024, filed Feb. 20, 2004, which claims priority under 35 U.S.C. §119 to Japanese Application 2003-50159 filed Feb. 26, 2003.

FIELD OF THE INVENTION

Warming the human body so as to improve the flow of blood and lymph fluid and to increase metabolism is well known. It is very effective for treatment of diseases and for overall health to warm affected parts or the entire body. Cancer cells are susceptible to heat, and will die out or be reduced in number when their temperature is several degrees higher than the body temperature.

As mentioned, it is effective to warm a local area of the human body, a relatively broad area thereof or the entire body. By using far-infrared rays, which are capable of warming not only a surface of the human body but also interior parts thereof, better results can be gained. The present invention relates to a far-infrared ray generator suitable for warming the human body.

BACKGROUND

As described in Japanese Patent Gazette No. 2000-140135, a heating apparatus includes a plurality of semicircular members, which are telescopically connected in an axial direction, and contains sheet heating elements including carbon black, which cover whole inner faces of the semicircular members. Electricity is applied to the sheet heating elements to heat until reaching 55-70° C. Further, another heating apparatus is disclosed in Japanese Patent Gazette No. 8-112302, in which sheet heating elements including carbon black are layered on inner faces of dome-shaped covers.

In the both apparatuses, a human body is placed in the dome-shaped covers or semicircular members, then far-infrared rays are irradiated toward the human body from the heating elements including carbon black so as to improve health, to treat cancers, etc.

Both apparatuses warm a broad area of the human body, e.g., the entire body from the neck down. Heating apparatuses capable of locally irradiating far-infrared rays are disclosed in Japanese Patent Gazettes No. 7-303709, 11-70175 and 2000-308668.

In a heating apparatus capable of entirely or locally warming the human body, the far-infrared ray generating sections include carbon black or tourmaline. However, if carbon black or tourmaline is solely used, the efficiency of generating far-infrared rays is low, and deep parts of the human body cannot be effectively warmed.

To warm deep parts of the human body, the heating apparatus must contact the surface of the human body for a long time or the temperature must be increased. However, if the heating apparatus is applied for a long time or the temperature of the heating apparatus is increased, the surface of the human body is overheated, such that the temperature of the surface of the human body reaches it's limit of endurance; the heating treatment must be stopped, and thermotherapy cannot be achieved.

In the case of diabetic patients, nerves are broken down, and may get burned.

To properly treat thermotherapy with a conventional heating apparatus, a therapist must have enough experience to adjust the temperature, apply the proper force for pressing the apparatus onto the human body and to adjust the moving speed of the apparatus. Further it takes a long time to gain curative effects.

Therefore, a modified heating apparatus, which can be easily used by unskilled therapists and which gives high curative effects, is required. A far-infrared ray generator, which is capable of efficiently generating far-infrared rays, is needed.

An object of the present invention is to provide a far-infrared ray generator, which is capable of efficiently generating far-infrared rays and effectively warm deep parts of the human body.

DESCRIPTION OF THE INVENTION

The object of the present invention is achieved by the following means. A far-infrared ray generator is provided comprising a far-infrared ray generating member used in a thermotherapy apparatus, which receives heat from a heating element and generates far-infrared rays, including only a radon generating rare element mineral, or at least two of a tourmaline mineral, carbon and a radon generating rare element mineral. By heating the far-infrared ray generating member, which includes only a radon generating rare element mineral, or at least two of a tourmaline mineral, carbon and a radon generating rare element mineral, with the heating element, the far-infrared ray generator efficiently generates far-infrared rays, so that deep parts of a human body can be efficiently warmed. Therefore, human health and thermotherapeutic effects can be highly improved. Namely, thermotherapy can be effectively performed with low temperature and in a short time, so that patients need not endure heat and their stress can be reduced. Further, the thermotherapy can be safely performed without burning the patients' skin.

Especially, by including both of the tourmaline mineral and the radon generating rare element mineral, the far-infrared rays can securely warm the deep part of the human body. By including all of the tourmaline mineral, the carbon and the radon generating rare element mineral, the far-infrared rays can be effectively generated so that deep parts of the human body can be effectively warmed. Further, in the case of using only the radon generating rare element mineral, its effect is superior to the case of using only tourmaline or only carbon. Therefore, in the case of generating far-infrared rays upon being heated by the heating element, only the radon generating rare element mineral may be properly used.

At least two of the tourmaline mineral, the carbon and the radon generating rare element mineral may be piled as layers, or powders of at least two of them may be mixed, so they may be optionally combined. The combinations can be applied to any types and sizes of far-infrared ray generators for warming the human body.

A far-infrared ray generator as described above wherein at least two of a tourmaline mineral, carbon and a radon generating rare element mineral are piled as layers is also provided. The tourmaline mineral, the carbon and the radon generating rare element mineral may be piled as layers. At least two of them may be layered.

By forming two or three layers of the tourmaline mineral, the carbon and the radon generating rare element mineral, the far-infrared rays are capable of warming deep parts of the human body. Each of the layers may be formed into powders and a solidified plate or sheet. The layers may be integrated or merely piled.

A far-infrared ray generator as described above, wherein powders of at least two of a tourmaline mineral, carbon and a radon generating rare element mineral are mixed, and the mixture is solidified with or without binders is also provided. This embodiment includes a structure, in which powders of the tourmaline mineral and the radon generating rare element mineral are mixed and the carbon works as the heating element.

By mixing powders of at least two of the tourmaline mineral, the carbon and the radon generating rare element mineral, the far-infrared ray generating member can be produced. In other embodiments, the mixture may be solidified with the binders.

By mixing powders of at least two of the tourmaline mineral, the carbon and the radon generating rare element mineral, the far-infrared ray generator is capable of warming deep parts of the human body. In the case of using the powders, the best combination is the powders of the tourmaline mineral and the radon generating rare element mineral.

A far-infrared ray generator as described above, wherein the far-infrared ray generating member includes only a radon generating rare element mineral, or at least two of a tourmaline mineral, carbon and a radon generating rare element mineral, and the far-infrared ray generating member is provided in a trowel-shaped main body and integrated with the heating element with or without a spacer is also provided.

In embodiments of the far-infrared ray generator described above, the far-infrared ray generating member includes only the radon generating rare element mineral, or at least two of the tourmaline mineral, the carbon and the radon generating rare element mineral, and the far-infrared ray generating member is provided in the trowel-shaped main body and integrated with the heating element with or without the spacer. When the far-infrared ray generating member is heated by the heating element, e.g., the electric heater, the far-infrared rays can efficiently warm deep parts of the human body. Further, the main body formed into the trowel-shape locally warms the human body, but it can easily be moved to a specific place and intensively warm there.

A far-infrared ray generator as described above wherein a far-infrared ray irradiating surface of the trowel-shaped main body is constituted by a glass plate having an outer convex face and an inner concave face, the far-infrared ray generating member is provided in the inner concave face, and the glass plate is formed into an elliptical shape, in which a long axis is about 8-20 cm, a short axis is about 4-9 cm and thickness is about 1.5-4 cm is also provided.

Since the far-infrared ray irradiating surface of the trowel-shaped main body is constituted by the glass plate having the outer convex face and the inner concave face and the far-infrared ray generating member is provided in the inner concave face, the outer convex face can be easily slid on the human body or a cloth covering the human body so that the thermotherapy can be easily performed. Further, the glass plate is formed into an elliptical shape in which the long axis is about 8-20 cm, the short axis is about 4-9 cm and thickness is about 1.5-4 cm, so the trowel-shaped main body can be easily inserted into and moved in narrow and complex places, e.g., armpits, or a space under a jaw. Therefore, affected parts can be irradiated by the far-infrared rays. If the main body is moved in a direction perpendicular to the long axis, a broad area can be warmed.

A far-infrared ray generator as described above wherein the heating element is provided on an outer side of a vibrating section, the far-infrared ray generating member including only a radon generating rare element mineral, or at least two of a tourmaline mineral, carbon and a radon generating rare element mineral is integrated with the heating element with or without a spacer is also provided.

Since the far-infrared ray generating member including only the radon generating rare element mineral, or at least two of the tourmaline mineral, the carbon and the radon generating rare element mineral is integrated with the heating element, which is provided on the outer side of the vibrating section, with or without a spacer, the vibrating section is capable of applying vibrations to the human body, so that muscles can be massaged and the far-infrared rays warm deep parts of the human body.

A far-infrared ray generator as described above wherein the heating element is provided on an inner side of a dome-shaped face, and the far-infrared ray generating member including only a radon generating rare element mineral, or at least two of a tourmaline mineral, carbon and a radon generating rare element mineral is provided on an outer side or an inner side of the heating element and integrated with the heating element with or without a spacer is also provided.

In embodiments of the far-infrared ray generator described above, the far-infrared ray generating member including only the radon generating rare element mineral, or at least two of the tourmaline mineral, the carbon and the radon generating rare element mineral is provided on the outer side or the inner side of the heating element and integrated with the heating element, which is provided on the inner side of the dome-shaped face, with or without the spacer; when the far-infrared rays irradiate the human body located in the dome-shaped face, a broad area of the human body can be efficiently irradiated by the far-infrared rays. Further deep parts of the human body can be warmed. Therefore, a broad area of the human body, e.g., the entire body from the neck down, can be suitably warmed. Since the far-infrared rays reach deep parts of the human body, temperature in the dome can be lowered, so that the patient need not endure high temperatures and can be treated for a longer time.

A far-infrared ray generator as described above wherein the far-infrared ray generator includes three far-infrared ray generators: the far-infrared ray generator having the vibrating section, which will be pressed onto a hot towel including herb components; the far-infrared ray generator having the trowel-shaped main body; and the far-infrared ray generator having the dome-shaped face. Note that, "herb" includes various medical plants.

Since the three far-infrared ray generators the far-infrared ray generator having the vibrating section, which will be pressed onto the hot towel including herb components, the far-infrared ray generator having the trowel-shaped main body and the far-infrared ray generator having the dome-shaped face are included, deep parts of the human body can be intensively warmed and a broad area of the human body, e.g., the entire body from neck down, can be deeply warmed by selecting the far-infrared ray generators. Further the far-infrared rays and herb components can be impregnated into the human body by vibrating the hot towel including the herb components with the removal of sweat by a hot towel.

When vibrations are applied to the hot towel with irradiation of the far-infrared rays, the far-infrared rays effectively heat the hot towel, so the temperature of the hot towel can be kept for a long time.

A method of irradiating far-infrared rays with a far-infrared ray generator, which includes only a radon generating rare element mineral, or at least two of a tourmaline mineral, carbon and a radon generating rare element mineral piled as layers, or mixed powders of at least two of a tourmaline mineral, carbon and a radon generating rare element mineral, which are solidified with or without binders is also provided. This embodiment comprises the steps of: (1) making the far-infrared ray generator having a trowel-shaped heating element contact a surface of a human body so as to make the human body absorb far-infrared rays; (2) placing the human body on the inner side of the far-infrared ray generator, which is provided on the inner side of a dome-shaped surface, so as to make the human body absorb the far-infrared rays; and (3) pressing the far-infrared ray generator, which is vibrated by a vibrating section, onto a hot towel including herb components, which has been put on the human body, wherein the step are executed in the order of (1)→(2)→(3).

When deep parts of the human body are warmed by the far-infrared ray generator, which includes only the radon generating rare element mineral, or at least two of the tourmaline mineral, the carbon and the radon generating rare element mineral, the method includes the steps of (1) making the far-infrared ray generator having the trowel-shaped heating element contact the surface of the human body so as to make the human body locally deeply a sorb far-infrared rays, then (2) placing the human body on the inner side of the far-infrared ray generator, which is provided on the inner side of the dome-shaped surface, so as to make a broad area of the human body, e.g., the entire body from the neck down, deeply absorb the far-infrared rays.

Therefore, an affected part can be securely intensively warmed. Further the entire human body can be warmed, so that health can be improved and the thermotherapy can be effectively and securely performed.

Finally, as described in the above step (3), vibrations are applied to the hot towel, which includes the herb components and which covers the human body, and the far-infrared rays are irradiated, so that the far-infrared rays and the herb components can be impregnated into the human body by vibrating the hot towel including the herb components with the removal of sweat by the hot towel.

A full course of the thermotherapy can be performed, namely health can be improved; the far-infrared rays can be locally and widely irradiated; sweat can be removed by the hot towel, the temperature can be kept by the far-infrared rays; the herb components can be impregnated into the human body; and the vibrations massage the body, so that the full course of thermotherapy makes the patient feel good.

PREFERRED EMBODIMENTS OF THE INVENTION

Figure 1:
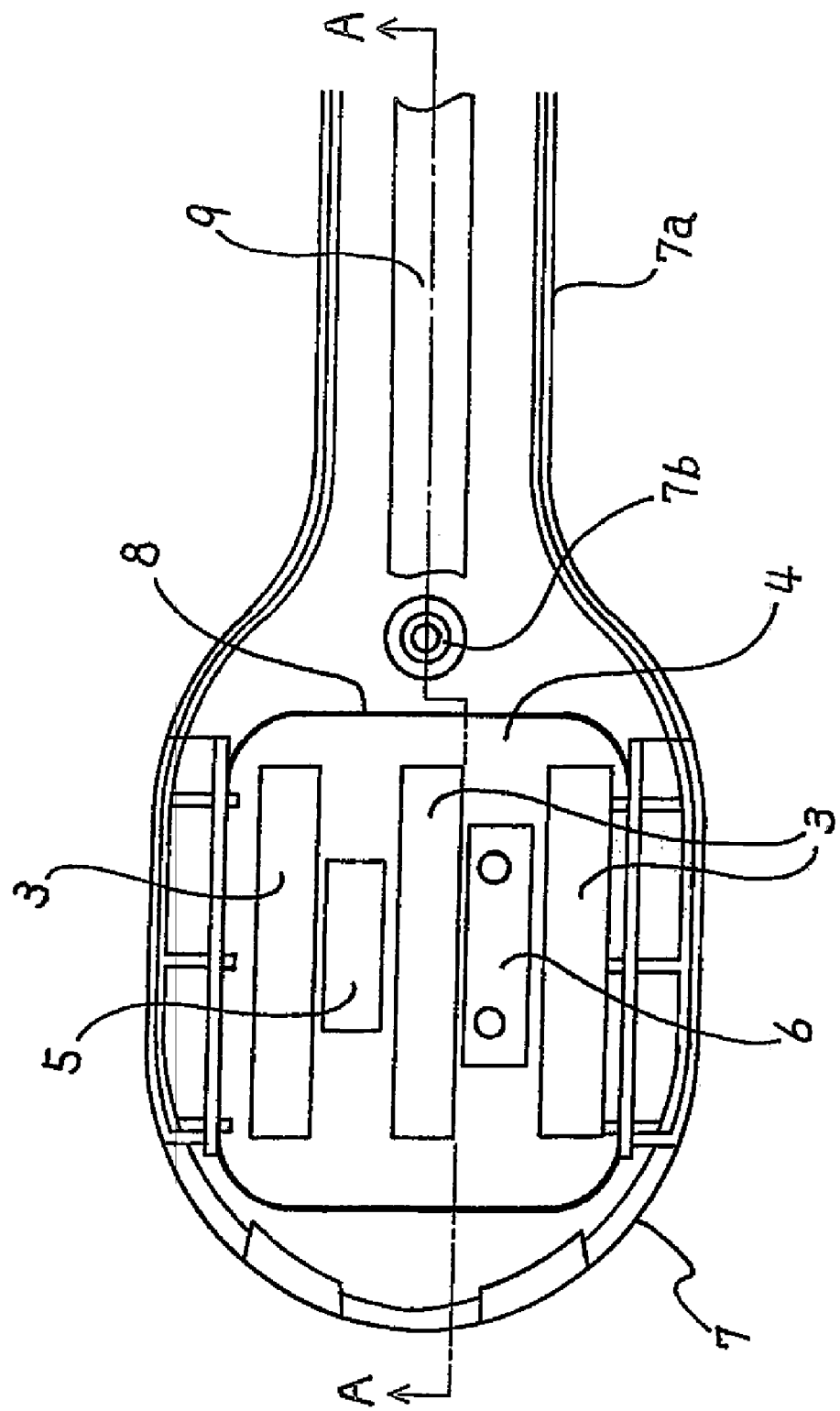
FIG. 1 is a plan view of a trowel-shaped far-infrared ray generator, wherein an inner mechanism is shown.
Figure 2:
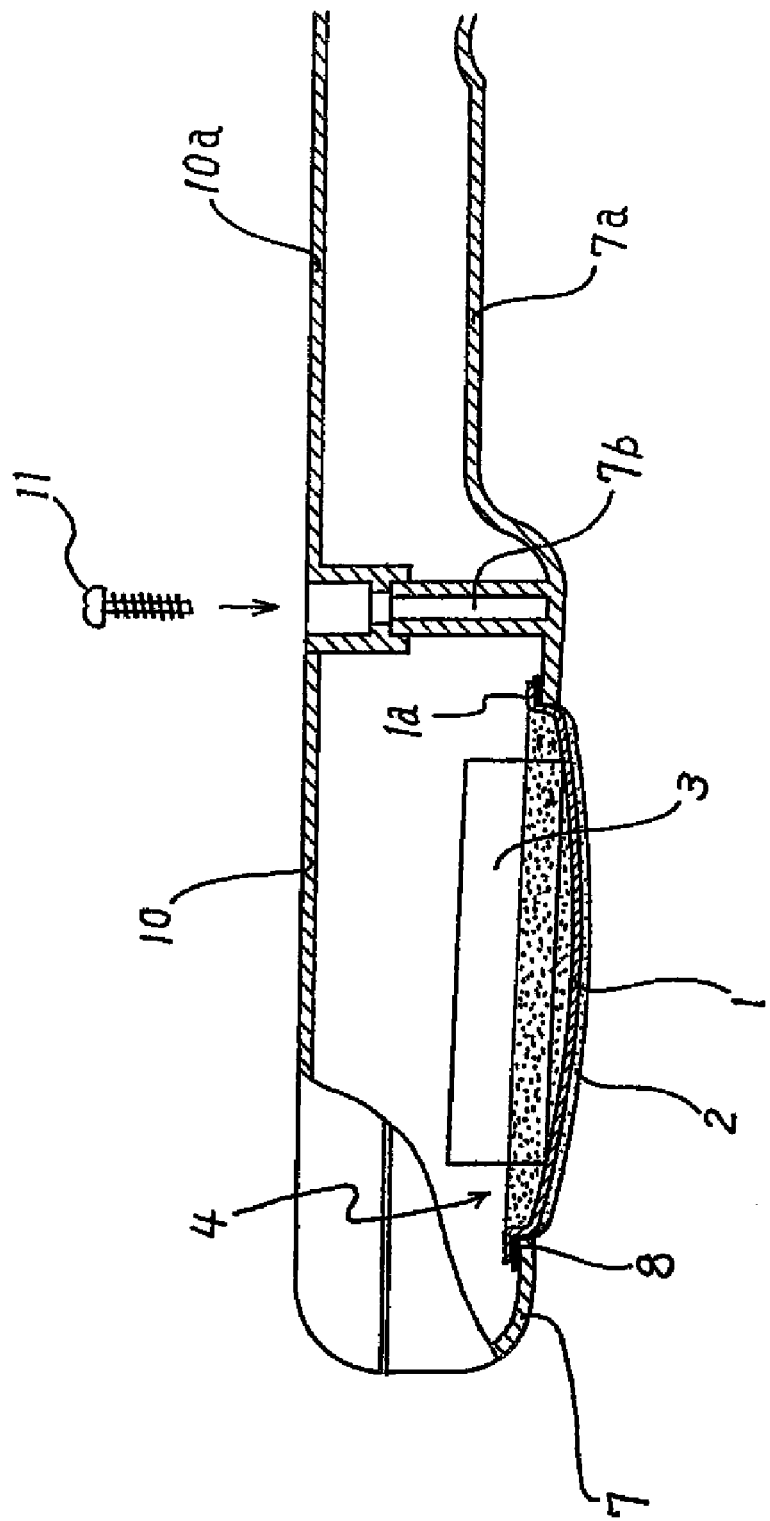
FIG. 2 is a sectional view taken a line A-A of FIG. 1.

Embodiments of the far-infrared ray generator and the method of irradiating far-infrared rays of the present invention will be further explained. FIGS. 1 and 2 show a trowel-shaped far-infrared ray generator, FIG. 1 is a plan view of an inner mechanism thereof, and FIG. 2 is a sectional view taken at line A-A of FIG. 1.

In the drawings, an outer face of a metal plate 1 is formed into a convex face, and a far-infrared ray generating section 2 is formed, as layers, on the convex face. The layers constituting the far-infrared ray generating section 2 are layered on the outer face of the metal plate 1, the convex face of the far-infrared ray generating section 2 will be pressed onto a surface of a human body for thermotherapy. Note that, a coat layer for smoothly sliding the far-infrared ray generating section 2 may be formed on the convex face. The metal plate 1 may be made of other materials, e.g., aluminum, stainless steel, glass.

Ceramic heaters 3 are adhered on an inner concave face of the metal plate 1 by, for example, epoxy resin 4. The number of ceramic heaters 3 is not limited, and they are separately arranged so as to uniformly heat a whole surface of the far-infrared ray generating section 2. A plate-shaped heater may be used instead of the ceramic heaters 3 so as to uniformly heat the far-infrared ray generating section 2.

A thermal fuse 5 and a thermistor 6 are provided between the ceramic heaters 3 and 3 and adhered to the metal plate 1 by epoxy resin 4. A plastic case 7 accommodates the ceramic heaters 3, the thermal fuse 5 and the thermistor 6. A window is opened to expose the far-infrared ray generating section 2, the outer convex face of the far-infrared ray generating section 2 is projected from the window, and an outer edge of the metal plate 1 is attached to an inner edge of the window by an insulating packing 8.

Power lines of the ceramic heaters 3, signal lines of the fuse 5 and the thermistor 6, etc. are passed through a code 9. A symbol 10 stands for a rear cover, and the rear cover 10 is fixed to the plastic case 7 by screwing screws 11 with screw holes 7b so that the outer edge 1a of the metal 1 is pressed onto the inner edge of the window by a press section of the rear cover. The code 9 is outwardly extended from the plastic case 7 to a power source via handle sections 7a and 10a.

In the far-infrared ray generator, as described above, the far-infrared ray generating section 2 is constituted by at least two of a tourmaline mineral, carbon and a radon generating rare element mineral. The tourmaline mineral, the carbon and the radon generating rare element mineral may be respectively formed into layers, or their powders may be mixed.

Two or three of the tourmaline mineral layer, the carbon layer and the radon generating rare element mineral layer are layered. Each of the layers may be formed into powders, a plate or a sheet. Combinations of the layers may be optionally selected, but the combination of the tourmaline mineral layer and the radon generating rare element mineral layer has optimum efficiency of irradiating far-infrared rays.

At least two of the tourmaline mineral powders, the carbon powders and the radon generating rare element mineral powders may be mixed. The mixture may be solidified and formed into a plate or a sheet by, for example, heat-resistance resin.

The plate or sheet-shaped far-infrared ray generating section 2 is piled on the surface of the metal plate 1 and adhered thereon by adhesive, so that the metal plate 1 and the far-infrared ray generating section 2 are layered. Resin including only the radon generating rare element mineral powders or at least two of the tourmaline mineral powders, the carbon powders and the radon generating rare element mineral powders may be applied or baked on the surface of the metal plate 1. The metal plate 1 may be made of other materials, e.g., aluminum, stainless steel.

The metal plate 1 may be omitted, the far-infrared ray generating section 2 may be formed into a convex shape, and the ceramic heaters 3, the thermal fuse 5 and the thermistor 6 may be fixed on an inner face thereof by resin. A glass plate may be used instead of the metal plate 1 so as to smoothly slide. In this case, the glass plate has an outer convex face, and the far-infrared ray generating section 2 may be applied or baked on an inner concave face thereof. The glass plate may be made of ordinary glass, preferably reinforced glass or crystallized glass having high toughness. A plate-shaped heater may be used instead of the ceramic heaters so as to uniformly heat the far-infrared ray generating section.

In the trowel-shaped far-infrared ray generator, the ceramic heaters 3 begin to generate heat when a power switch is turned on, then the heat is conducted to the epoxy resin 4, the metal plate 1 and the far-infrared ray generating section 2, so that the far-infrared ray generating section 2 is heated. The thermistor 6 controls temperature.

The thermistor 6 maintains temperature of the far-infrared ray generating section 2 at, for example, 50° C., 60° C., 70° C. or 80° C. If the temperature rises to, for example, 10° C. or more, higher than the prescribed temperature, the thermal fuse 5 turns off the power source of the ceramic heaters 3.

When a user uses the trowel-shaped far-infrared ray generator, the user grips the handle sections 7a and 10a and presses the convex face of the far-infrared ray generating section 2 onto an affected part of a human body so as to irradiate the far-infrared rays to a deep part of the human body. The far-infrared ray generator is properly moved on the human body so as not to overheat the human body.

As described above, the far-infrared ray generating section 2 of the trowel-shaped far-infrared ray generator includes at least two of the tourmaline mineral, the carbon and the radon generating rare element mineral, so its far-infrared ray irradiating efficiency is higher than that of a far-infrared ray generator, which includes only the tourmaline mineral, only the carbon or only the radon generating rare element mineral; therefore, the far-infrared ray generator of the present embodiment is capable of efficiently irradiating far-infrared rays and warming deep parts of the human body.

Figure 3:
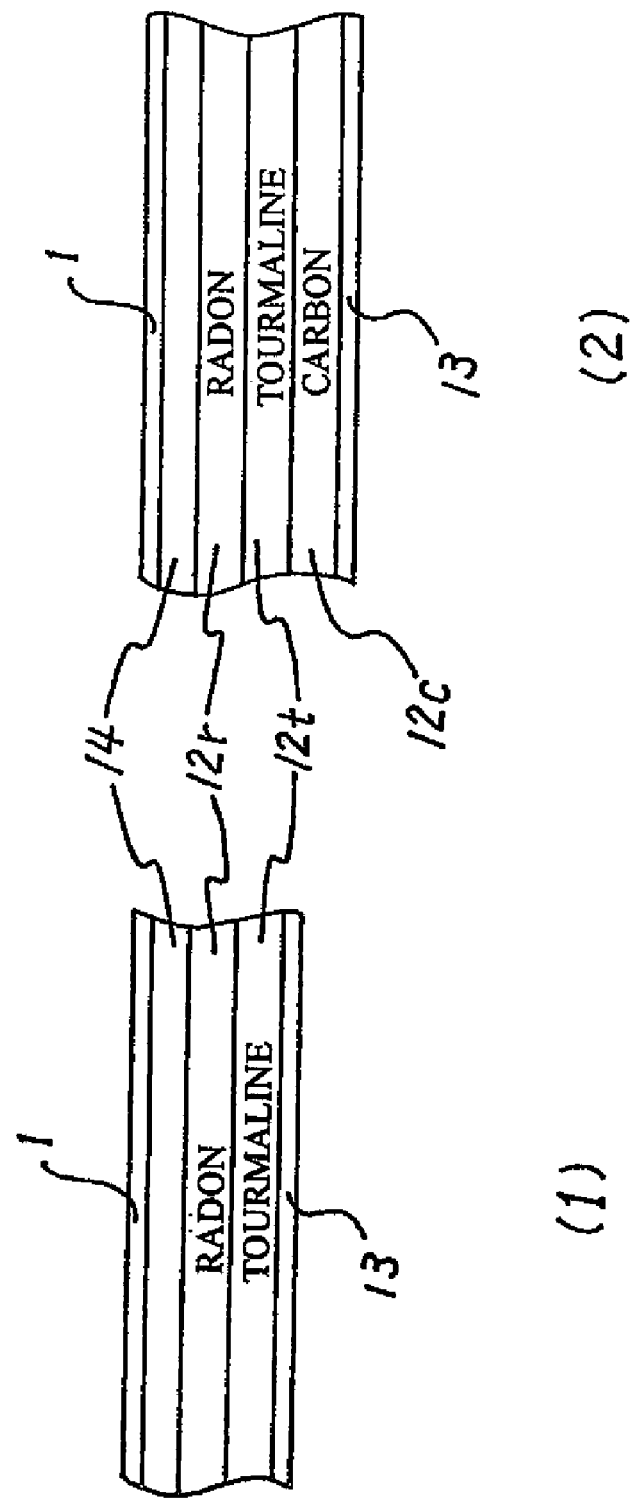
FIG. 3 shows schematic views of far-infrared ray generating layers having layered structures.
Figure 4:
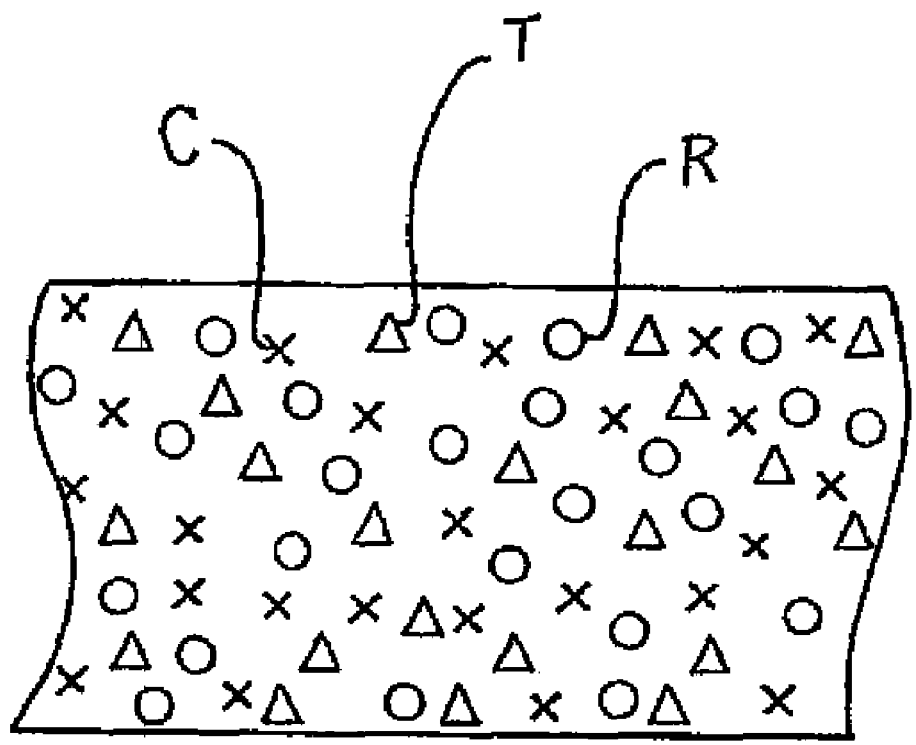
FIG. 4 is a schematic view of a far-infrared ray generating layer having a mixed structure.

Concrete examples of the far-infrared ray generating section 2 including three of the tourmaline mineral, the carbon and the radon generating rare element mineral, are shown in FIGS. 3 and 4. FIG. 3 shows schematic views of far-infrared ray generating sections having layered structures; FIG. 4 is a schematic view of a far-infrared ray generating section having a mixed structure.

The tourmaline mineral means known tourmaline called "electric stone". The tourmaline mineral generates negative ions and effectively irradiates far-infrared rays.

The radon generating rare element mineral is powders of rare element mineral including various elemental components, e.g., radium, thorium, generates colorless and odor-free inert gas elements, e.g., radon, thoron, and negatively-ionizes air. The radon generating rare element mineral may be selected from natural minerals, further mineral deposits of hot springs may be used as the radon generating rare element mineral. According to results of experiments performed by the inventor, the radon generating rare element mineral more efficiently irradiated far-infrared rays than tourmaline mineral and carbon. Preferable carbon is wood charcoal powders or bamboo charcoal.

In FIG. 3, (1) shows the layered structure, in which two of the tourmaline mineral, the carbon and the radon generating rare element mineral are optionally combined; (2) shows the layered structure including three of the tourmaline mineral, the carbon and the radon generating rare element mineral.

In FIG. 3(1), a tourmaline layer 12t and a radon generating rare element mineral layer 12r are layered, and they may be adhered or merely piled. The radon generating rare element mineral layer 12r is piled on the metal plate 1 or adhere thereto by adhesive 14. A lubricating layer 13 may be applied or piled on surface of the tourmaline layer 12t so as to protect the far-infrared ray generating section 2 and easily slide. Preferably, the lubricating layer 13 is made of synthetic resin.

On the other hand, the radon generating rare element mineral layer 12r may be provided on the outer side, and the tourmaline layer 12t may be provided on the inner side. The layered structure may be a two layered structure constituted by the tourmaline layer 12t and a carbon layer, or a two layered structure constituted by the radon generating rare element mineral layer 12r and the carbon layer. In both cases, any layers may be provided on the outer side.

In the three layered structure shown in FIG. 3(2), the radon generating rare element mineral layer 12r, the tourmaline layer 12t and a carbon layer 12c are layered in that order from the metal plate 1. In this case too, the layers may be optionally arranged.

The radon generating rare element mineral layer 12r, the tourmaline layer 12t and the carbon layer 12c may be respectively formed into plates or sheets, further the plates or sheets may be formed by solidifying powders. The powders may be solidified with binders, e.g., synthetic resin, so as to form into the plate or sheet. Note that, thickness of the layers 12r, 12t and 12c are not limited, but preferable total thickness of the three layers is about 1-5 mm. The total thickness is not limited to that value, and it is determined on the basis of use and size of the far-infrared ray generator.

In FIG. 4, powders of the tourmaline mineral, the carbon and the radon generating rare element mineral are mixed. In FIG. 4, ○ is a powder of the radon generating rare element mineral; Δ is a powder of the tourmaline; × is a powder of the carbon. The mixture of those powders is shown in FIG. 4. When the mixture is used, the mixture shown in FIG. 4 may be formed into a plate or sheet and combined with a heating element, or the mixture shown in FIG. 4 may be mixed with binders, e.g., synthetic resin, to solidify.

In the case shown in FIG. 2, in which the mixture is layered on the metal plate 1, the mixed powders including binders, e.g., synthetic resin, may applied on the surface of the metal plate 1, or the mixed powders, which has been previously formed into a plate-shape or a sheet-shaped, may be layered thereon. Further, a lubricating layer may be formed on an outer face of the far-infrared ray generating section 2 so as to protect the far-infrared ray generating section and easily slide.

Next, effects of using three layers the tourmaline layer, the radon generating rare element mineral layer and the carbon layer will be explained with reference to TABLE 1. In TABLE 1, curative effects of six far-infrared ray means of the present invention, each of which included said three layers, and three conventional far-infrared ray means are shown.

the conventional far-infrared means did not include the three substances used in the present invention, and they showed insufficient curative effects.

Figure 8:
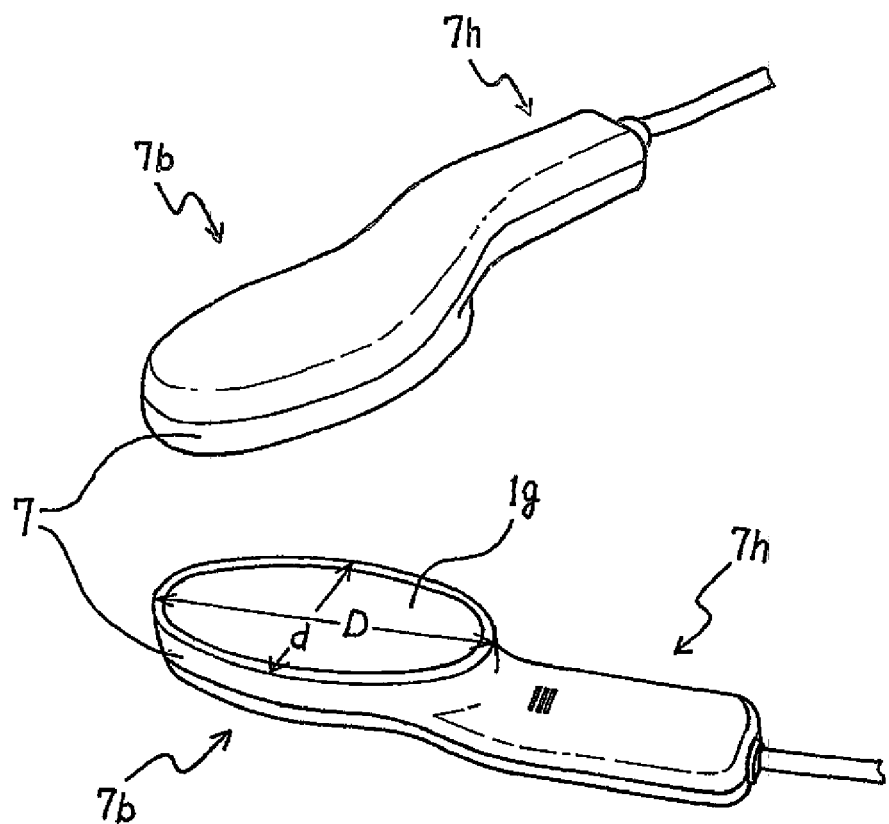
FIG. 8 shows a modified trowel-shaped far-infrared ray generator shown in FIGS. 1 and 2, wherein (1) is a perspective view seen from a rear side, (2) is a perspective view seen from a far-infrared ray irradiating side, and (3) and (4) are sectional views of a convex glass plate.
Figure 8:
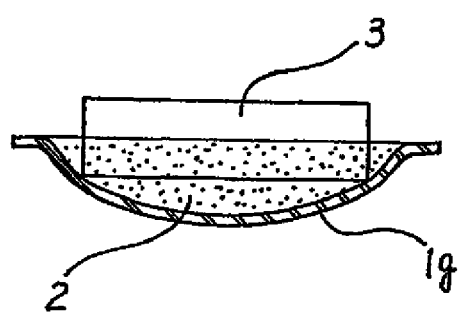
Figure 8:
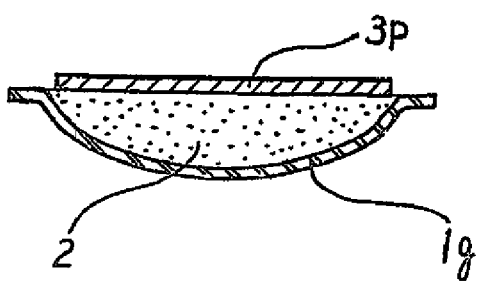

FIG. 8 shows a modified far-infrared ray generator shown in FIGS. 1 and 2, (1) is a perspective view seen from a rear side, and (2) is a perspective view seen from a far-infrared ray irradiating side, which will be pressed onto a human body. In the far-infrared ray generator, a glass plate 1g has an outer convex face, which contacts the human body, and a far-infrared ray generating member made of the three substances is provided on an inner concave face thereof. The glass plate 1g is formed into an elliptical shape, and its outer edge is covered with a plastic case 7. The plastic case 7 constitutes a main body of the far-infrared ray generator and

TABLE 1

Curative Effects

| | Samples of The Embodiment | | | | | | Comparative Samples | | |
|---|---|---|---|---|---|---|---|---|---|
| | 1 | 2 | 3 | 4 | 5 | 6 | 1 | 2 | 3 |
| Tourmaline Mineral <0.075 m/m> | 3 | 7 | 11 | 15 | 3 | 15 | — | — | — |
| Wood Charcoal (Carbon) <0.075 m/m> | 3 | 7 | 11 | 15 | 3 | 15 | — | — | — |
| Radon Generating Rare Element Mineral <0.075 m/m> | 3 | 7 | 11 | 15 | 3 | 15 | — | — | — |
| Softening Point 870° C. Glass Component <0.075 m/m> | | | | 55 | | | 100 | | |
| Softening Point 833° C. Glass Component <0.075 m/m> | | | 67 | | | | | | |
| Softening Point 645° C. Glass Component <0.075 m/m> | | 79 | | | | | | | |
| Softening Point 627° C. Glass Component <0.075 m/m> | 91 | | | | | | | 100 | |
| Thermosetting Epoxy Resin | | | | | | | | | 100 |
| SUS304 Metal Plate (Thickness 1.0 m/m) | | | ○ | ○ | | | ○ | | |
| Aluminum Plate (Thickness 1.0 m/m) | ○ | ○ | | | ○ | ○ | | ○ | ○ |
| Set Temperature of Heating Element (° C.) | 75 | 75 | 75 | 75 | 75 | 75 | 75 | 75 | 75 |
| Performed by Unskilled Therapist | ○ | ○ | ○ | ○ | ○ | ○ | ○ | ○ | ○ |
| Time of Thermotherapy (Min.) | 10 | 10 | 10 | 10 | 10 | 10 | 10 | 10 | 10 |
| Curative Effects to Stiff Neck (A Plurality of Patients) | | | | | | | | | |
| High Effect | | | ○ | ○ | | ○ | | | |
| Medium Effect | ○ | ○ | | | ○ | | | | ○ |
| Low Effect | | | | | | | | ○ | |
| No Effect | | | | | | | ○ | | |

In TABLE 1, numeric values of the tourmaline mineral, the wood charcoal (carbon), the radon generating rare element mineral, the glass component and the thermosetting epoxy resin were blending quantities (weight part).

Note that, the conventional far-infrared means of the comparative samples were formed like trowel-shapes shown in FIGS. 1 and 2. The samples of the invention and the comparative samples were used under the same conditions: the set temperature of the heating elements, the therapist, the time of thermotherapy and patients who had experienced the thermotherapy several times.

According to the results, the samples 1-6 of the invention, in each of which the far-infrared ray means includes the three layers: the tourmaline layer, the carbon layer and the radon generating rare element mineral layer, gave enough curative effects. Further, in each of the samples, the curative effects were improved with increasing the quantities of tourmaline, carbon and radon generating rare element mineral.

Note that, the glass component for baking the far-infrared generating section 2 and the epoxy resin for adhering the same did not badly influence the curative effects of the thermotherapy. The three substances of TABLE 1 had functions of the thermotherapy, and the functions were improved by combining said substances. The comparative samples of accommodates heaters and circuit elements. A long axis D of the main body 7b is 13.5 mm, but it may be about 8 cm for a small size generator; it may be about 20 cm for a large size generator. A short axis d thereof is about 7 cm, but it may be about 4 cm for the small size generator; it may be about 9 cm for the large size generator. Thickness there of is about 2.5 cm, but it may be about 1.5 cm for a thin generator; it may be about 4 cm for a thick generator. A space about 1.5-3 cm is formed between the main body and a handle 7h, so that no fingers of a user gripping the handle contact the patient. Namely, a step-shaped section is formed therebetween.

Since the long a is of the trowel-shaped main body 7b, in which the far-infrared ray generating section, the heaters, the circuit elements, etc. are accommodated, is 8-20 cm, the short axis thereof is about 4-9 cm, the thickness thereof is about 1.5-4 cm, the main body can be easily inserted into narrow parts or complex-shaped parts of the human body, e.g., arm pits, a space between legs, a space under a jaw, rear spaces of ear lobes, and slid, so that the far-infrared ray generator can securely irradiate far-infrared rays to affected parts of the human body. In the present embodiment, thickness of the glass plate 1g is 2 mm, a radius of a circle on the long axis side is 355 mm; a radius of a circle on the short axis side is 78 mm. Therefore, the glass plate is formed like a dome-shape as a whole, and a center part of the inner concave face is the deepest part. Note that, a rear face of the main body 7b may be a flat face or a slight convex face.

In FIG. 8, (3) and (4) are sectional views of the convex glass plate 1g, which is a slippery glass and used instead of the metal plate 1 shown in FIGS. 1 and 2. In the present embodiment, the outer convex face of the glass plate 1g is exposed, the inner face thereof is the concave face. The far-infrared ray generating section 2 is provided in the inner concave face and contacts a heater. As shown in (3), the heater 3, which is the ceramic heater shown in FIGS. 1 and 2, is embedded in the far-infrared ray generating section 2 provided in the inner concave face and adhered by an adhesive. On the other hand, as shown in (4), an inner face of the far-infrared ray generating section 2 (the face opposite to the glass plate 1g) may be flat, and a plate-shaped heater 3p may be piled thereon. A heating element of the heater 3p is patterned n a flat plate, the entire surface of the far-infrared ray generating section 2 can be uniformly heated by piling the heater thereon. Note that, preferable thickness of the glass plate 1g is about 1-3 mm.

Since the convex glass plate 1g is the contact and slide part, the far-infrared ray generator is capable of easily and smoothly sliding on the surface of the affected part of the human body or cloth covering the human body. In the case shown in FIG. 2, heat conductivity of the metal plate 1 is high, and the far-infrared ray generating section 2 is thin, so the heat generated by the heaters are directly transmitted to the human body and excessively warm the human body. Therefore, thermal stimulation is too strong for cancer patients, old patients, patients having delicate skin, etc., so that sufficient curative effects cannot be obtained.

On the other hand, heat conductivity of the glass plate is lower than that of the metal plate, and the thickest part of the far-infrared ray generating section 2, which corresponds to the deepest part of the inner concave face, is at least about 3-8 mm, so the heat generated by the heater is slowly transmitted to the human body. When the glass plate contacts the human body and temperature of the glass plate 1g falls, unlike the metal plate which is immediately heated by the heater, the glass plate is slowly heated. Therefore, the patient feels hot for a quick moment when the glass plate contacts the human body, but the heat is slowly or softly transmitted to the human body, so that applying excessive thermal stimulation to the patient can be prevented.

TABLE 2 shows curative effects of the modified far-infrared ray generator, each of which included the convex glass plates; unlike TABLE 1, the convex glass plate 1g shown in FIG. 8 was employed, and effects of the far-infrared ray generating section, each of which included the three substances: tourmaline mineral, wood charcoal (carbon) and radon generating rare element mineral, are added.

TABLE 2

Curative Effects of The Modified Far-infrared Ray Generator

| | Samples of The Invention (No.) | | | | | | | Comparative Conventional Samples | | |
|---|---|---|---|---|---|---|---|---|---|---|
| | 1 | 2 | 3 | 4 | 5 | 6 | 7 | 1 | 2 | 3 |
| Tourmaline Mineral <0.075 m/m> | 3 | 7 | 11 | 15 | 2 | 5 | 7 | — | — | — |
| Wood Charcoal (Carbon) <0.075 m/m> | 3 | 7 | 11 | 15 | 2 | 5 | 7 | — | — | — |
| Radon Generating Rare Element Mineral <0.075 m/m> | 3 | 7 | 11 | 15 | 2 | 5 | 7 | — | — | — |
| Softening Point 678° C. Glass Component <0.075 m/m> | | | | 55 | | | | | | |
| Softening Point 653° C. Glass Component <0.075 m/m> | | | 67 | | | | | | | |
| Softening Point 636° C. Glass Component <0.075 m/m> | | 79 | | | | | | | | |
| Softening Point 627° C. Glass Component <0.075 m/m> | 91 | | | | | | | | | |
| Thermosetting Epoxy Resin | | | | | 97 | 85 | 79 | | | |
| SUS304 Metal Plate (Thickness 1.0 m/m) | | | ○ | ○ | ○ | | | ○ | | |
| Aluminum Plate (Thickness 1.0 m/m) | ○ | ○ | | | | ○ | | | ○ | |
| Glass Plate (Thickness 1.0 m/m) | | | | | | | ○ | | | ○ |
| Set Temperature of Heating Element (° C.) | 75 | 75 | 75 | 75 | 75 | 75 | 75 | 75 | 75 | |
| Performed by Unskilled Therapist | ○ | ○ | ○ | ○ | ○ | ○ | ○ | | | |
| Time of Thermotherapy (Min. for Each Therapy) | 10 | 10 | 10 | 10 | 10 | 10 | 10 | | | |
| Number of Times of Thermotherapy | | | | | | | | | | |
| Curative Effects to Stiff Neck (A Plurality of Patients) | | | | | | | | | | |
| High Effect | | | ○ | ○ | | ○ | ○ | | | |
| Medium Effect | ○ | ○ | | | | | | | | |
| Low Effect | | | | | ○ | | | | ○ | ○ |
| No Effect | | | | | | | | ○ | | |

Figure 9:
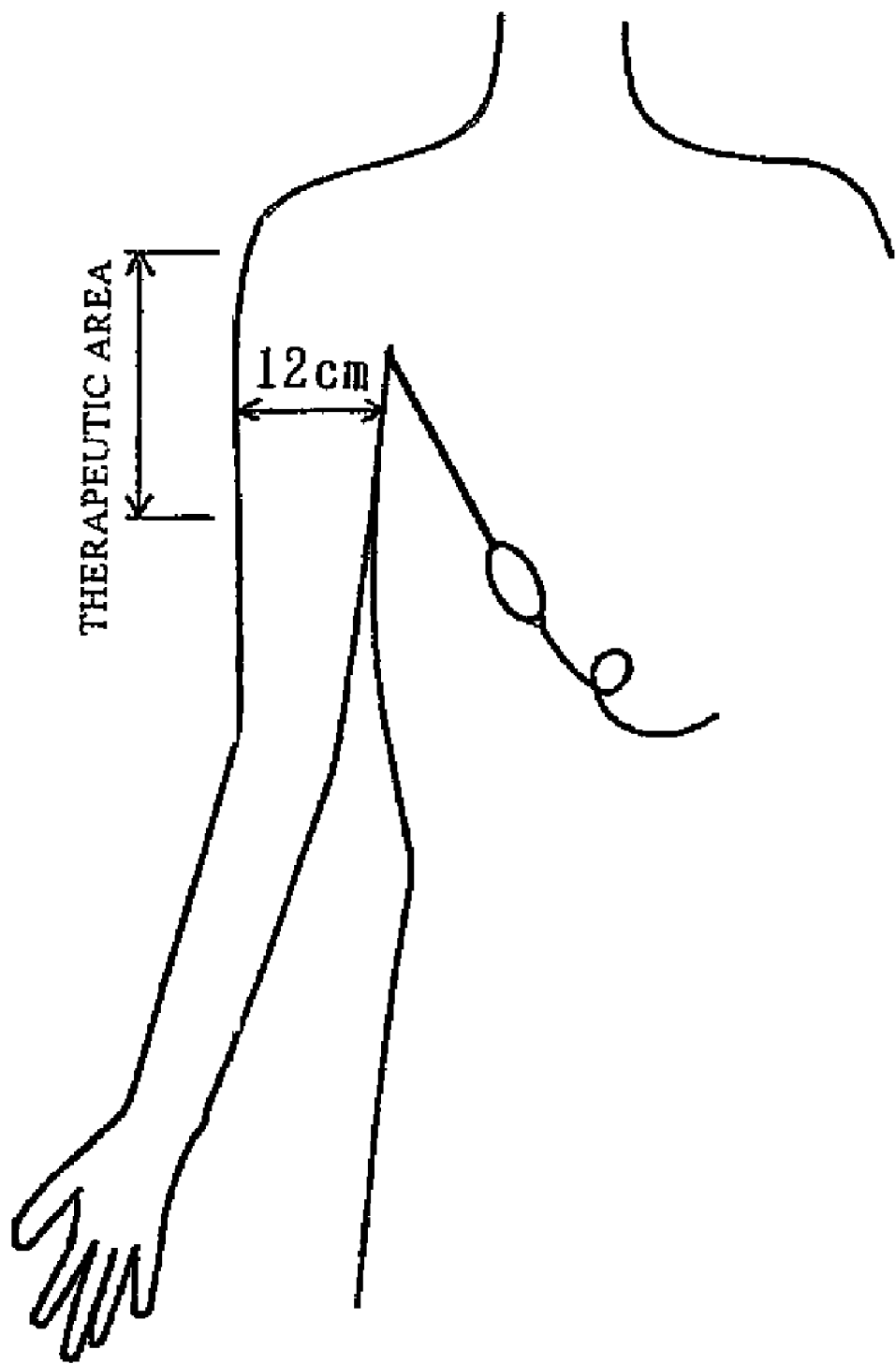
FIG. 9 is an explanation view showing a method of measuring body temperature and measuring points.
Figure 10:
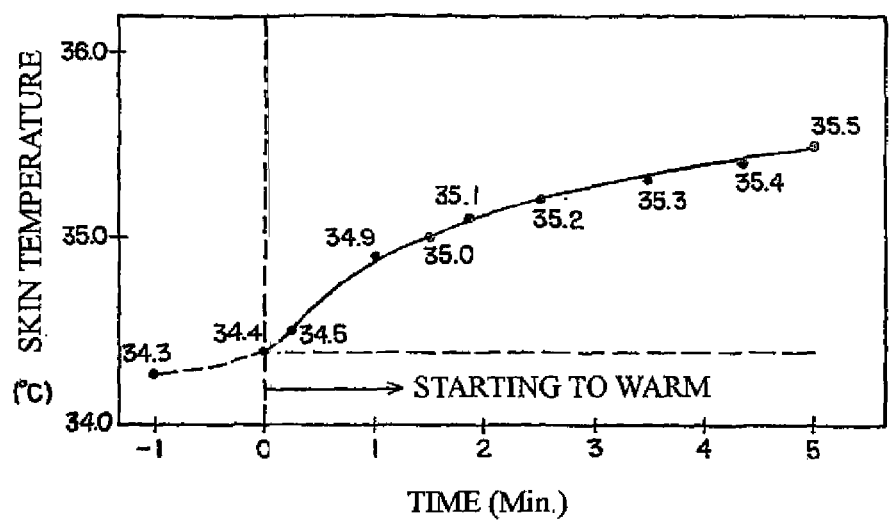
FIG. 10 is a graph of body temperature measured at arm pit.

As clearly shown by TABLE 2, the sample 7 gave enough curative effects of stiff neck, and far-infrared rays irradiated therefrom were measured. A method of measuring the far-infrared rays and measuring points are shown in FIG. 9; namely, a thermocouple was held under an arm, the far-infrared ray generator was pressed on an outer surface of the arm and slid within a therapy area. As shown in FIG. 10, temperature of an inner surface of the arm rose 1° C. for five minutes. Therefore, the heat was deeply transmitted from the outer surface of the arm to the inner surface thereof. Note that, diameter of the arm was about 12 cm, and thickness of the thermocouple was 1 mm.

Figure 11:
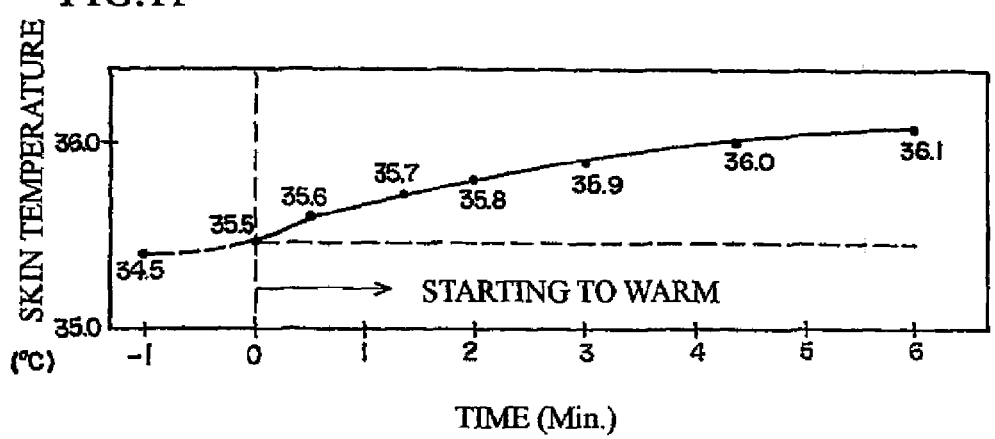
FIG. 11 is a graph of body temperature measured at chest.

FIG. 11 indicate rising skin temperature (° C.) of an adult examinee (male), wherein a thermocouple having thickness of 1 mm was fixed on a right chest of the exam nee by an adhesive tape, the examinee laid on a bath towel and the thermotherapy was treated on his back. According to the graph, the temperature rose about 0.5° C. for about six minutes. Therefore, the heat was transmitted in such thick chest. Dotted lines of FIGS. 10 and 11 shows the temperature varied by the conventional heat generator, and they are almost flat. According to the results, the far-infrared ray generator of the present invention is capable of warming a deep part of the human body, whose depth is 10-20 cm or more.

In the above described embodiment, the three substances of the tourmaline mineral, the carbon and the radon generating rare element mineral are mixed and embedded in the inner face of the convex glass plate, but the two of the tourmaline mineral and the radon generating rare element mineral may be mixed and embedded and the carbon may be used as the heater. The substances may be layered in the inner concave face of the glass plate. Especially, if the glass plate is formed into a half-barrel, they may be easily layered therein.

As described above, by employing the three substances of the tourmaline mineral, the wood charcoal (carbon) and the radon generating rare element mineral, far-infrared rays can be effectively generated and deep parts of the human body can be warmed. Besides the trowel-shaped far-infrared ray generator for intensively irradiating the affected part of the patient, the far-infrared ray generator of the present invention may be formed into a dome shape so as to deeply warm a broad area of the human body, e.g., entire body from neck down. Further, the far-infrared ray generator of the present invention, which includes an electric driven vibrating section, is capable of applying vibrations to the human body through a hot towel including herb components, which covers the human body, and the above described three therapies can be combined as a full course of thermotherapy.

Figure 5:
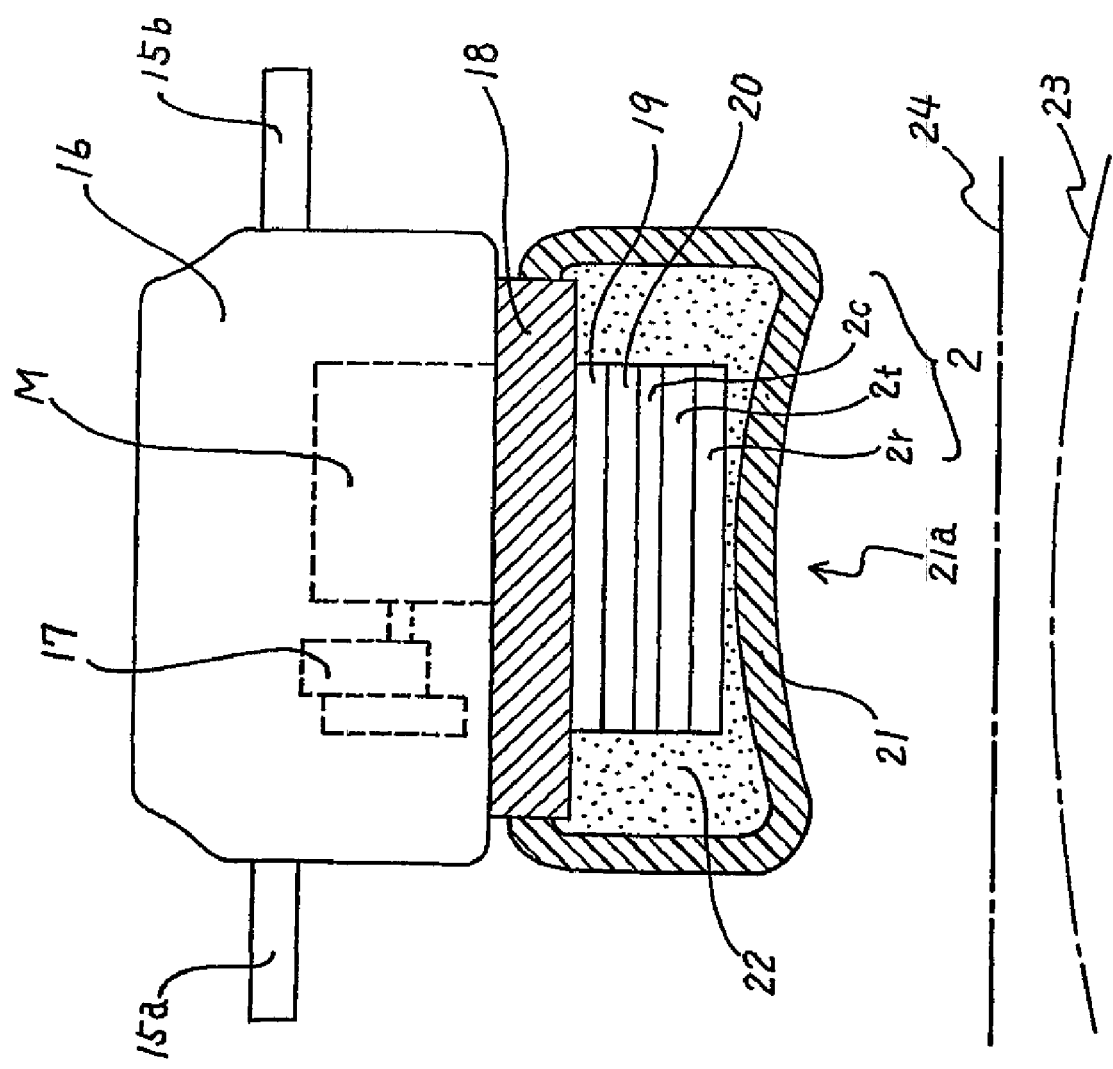
FIG. 5 is a sectional view of a far-infrared ray generator capable of applying vibrations.

A sectional view of another embodiment of the far-infrared ray generator, which includes vibration means, is shown in FIG. 5. Grips (handles) 15a and 15b are provided to both sides of a main case 16, in which a balance weight 17 for generating vibrations and a motor M for actuating the balance weight are accommodated.

A metallic vibration plate 18, which is vibrated by vibrating the balance weight 17, is provided outside of the main body 16, and a heater 20 is attached to the vibration plate 18 together with a heat insulator 19.

A thermo control circuit is connected to the heater 20 as well as the far-infrared generator shown in FIGS. 1 and 2. The heater is a small and vibration-resisting heater, e.g., silicon rubber heater, mold press heater.

The far-infrared ray generating section 2 is layered on the heater 20. Namely, the carbon layer 2c, the tourmaline layer 2t and the radon generating rare element mineral layer 2r are layered on the surface of the heater 20 in that order. The carbon layer 2c may be cloth, felt or paper including carbon fibers. The tourmaline layer 2t may be cloth, felt or paper including tourmaline mineral. The radon generating rare element mineral layer 2r may be made of a dried and solidified substance, which includes radium, radon, etc. and which is collected from radioactive spring.

The layered far-infrared ray generating section is wholly covered with a cover 21, which is made of, for example, urethane rubber, and an inner space is filled with a filler 22, e.g., epoxy resin. Note that, the carbon layer 2c, the tourmaline layer 2t and the radon generating rare element mineral layer 2r may be previously layered and integrated to form the far-infrared ray generating section 2.

When the vibration-type far-infrared ray generator is used, a user grips the handles 15a and 15b, a bottom face 21a of the cover 21 is pressed onto a human body, the motor M is started to generate vibrations; therefore, the vibrations massage the human body and the far-infrared ray generating section 2 irradiates infrared-rays so as to warm a deep part of the human body. The far-infrared ray generator is moved by both hands of the user, so that an affected part of the human body can be intensively irradiated with the far-infrared rays.

If a hot towel 24 is placed on the human body 23 and the vibrations and far-infrared rays are applied through the hot towel, curative effects can be improved. If a liquid including herb or medical plant components is penetrated in the hot towel, the herb or medical plant components can be incorporated in the human body by vibrations, so that the human body can be healed by the synergistic effects of the massage effect, the herb or medical plant effect and the far-infrared ray effect.

Figure 6:
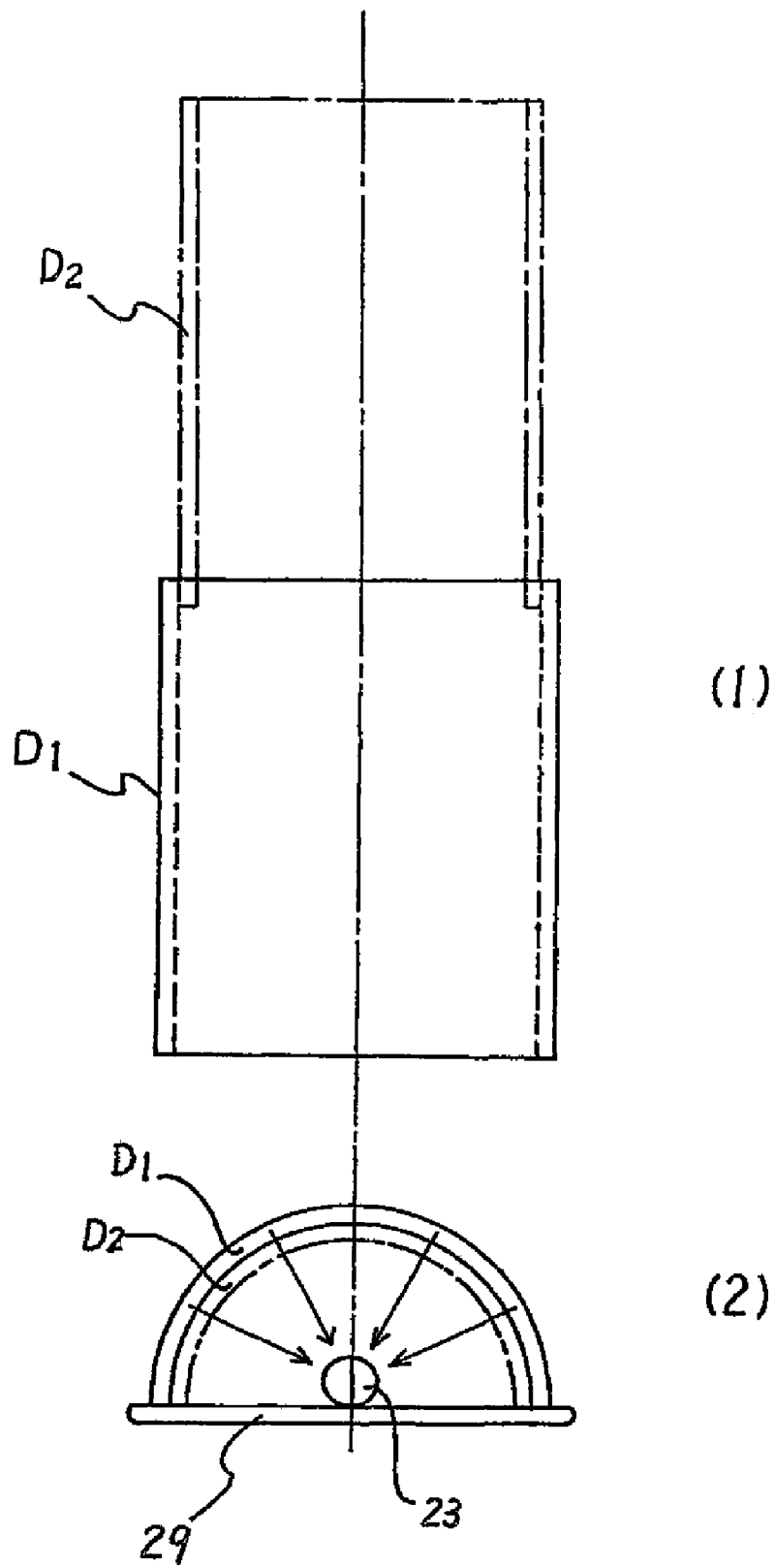
FIG. 6 shows dome-shaped far-infrared ray generators, wherein (1) is a plan view and (2) is front view.

Further, sweat of the human body can be absorbed and removed by the hot towel 24; if the far-infrared ray generator is used with the hot towel after the thermotherapy performed by the trowel-shaped far-infrared ray generator shown in FIGS. 1 and 2 or the dome-shaped far-infrared ray generators shown in FIG. 6, the thermotherapy can be further performed and sweat can be removed so that the patient can feel good. Namely, the far-infrared ray generator may be suitably used in the final stage of thermotherapy.

FIG. 6 shows the dome- or tunnel-shaped far-infrared ray generators, (1) is a plan view and (2) is a front view. Symbols D1 and D2 stand for dome-shaped or half-cylindrical-shaped far-infrared ray generators, and the small dome D1 can be accommodated in the large dome D2. Diameter of the large dome D1 is slightly greater than that of the small dome D2. To warm a main body part of the human body 23, one of the domes D1 and D2 may be used; to warm the entire body including tips of toes, end parts of the domes D1 and D2 are overlapped as shown in (1) so as to warm the human body by the both dome D1 and D2.

Figure 7:
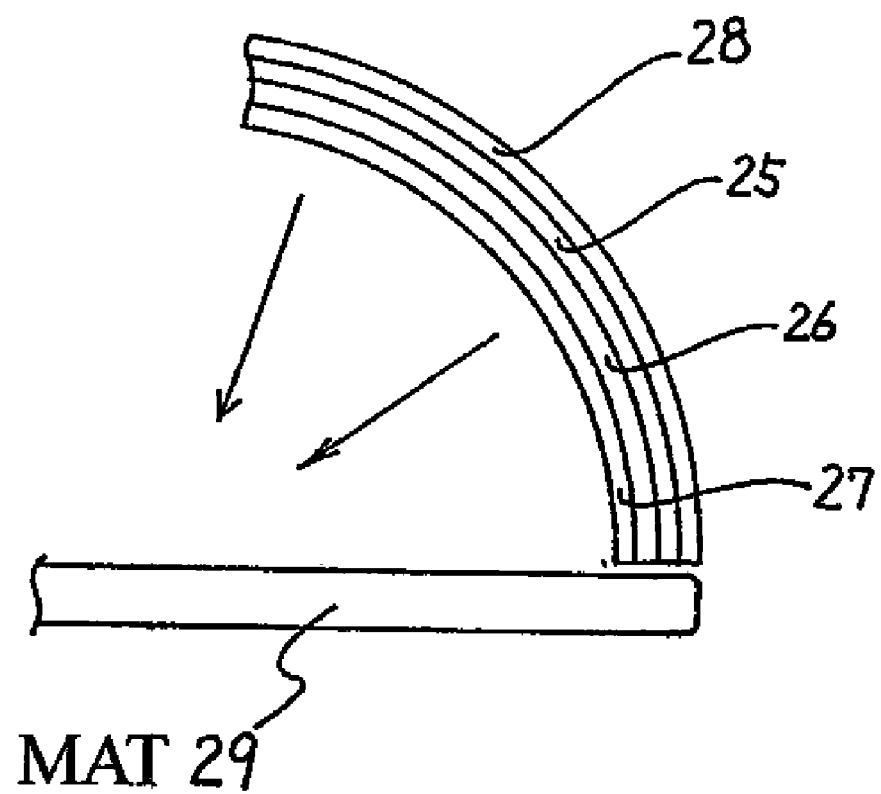
FIG. 7 is a sectional view of a part of a dome section.

As shown in FIG. 7, which is an enlarged view of a part of the dome D1 or D2, the dome has a layered structure. A heater layer 25 and a far-infrared ray generating layer 26, which is provided inside of the heater layer, are essential layers, and they are formed into half-cylindrical shapes. The heater layer 25 may be provided inside of the far-infrared ray generating layer 26.

In the far-infrared ray generating layer 26 provided inside of the heater layer 25, the carbon layer, the tourmaline layer and the radon generating rare element mineral layer are layered in that order as well as the vibration-type far-infrared ray generator shown in FIG. 5. The carbon layer may be cloth, felt or paper including carbon fibers. The tourmaline layer may be cloth, felt or paper including tourmaline mineral. The radon generating rare element mineral layer may be made of a dried and solidified substance, which includes radium, radon, etc. and which is collected from radioactive spring.

A protection layer 27 may be formed on an inner face of the far-infrared ray generating layer 26 if required. A surface of the protection layer 27 on the far-infrared ray generating layer 26 side is made of a buffer material, e.g., cotton cloth, felt; the other surface thereof on the inner space side is made of an inter or material, e.g., cotton cloth, vinyl leather.

Another protection layer 28 may be formed on an outer surface of the heater layer 25 if required. The protection layer 28 is constituted by a heat insulating layer, a heat-reflecting plate, a buffer layer and an exterior layer, which are layered on the heater layer 25 in that order. The heat insulating layer is made of, for example, cloth, felt and paper; the heat-reflecting plate is a stainless steel plate having thickness of about 1 mm; the buffer layer is made of cotton cloth or felt; and the exterior layer is made of cotton cloth or vinyl leather as well as the interior material.

To prevent overheating of the far-infrared ray generating layer 26, a heat insulating layer, which is made of, for example, cloth, felt and paper, may be provided between the heater layer 25 and the far-infrared ray generating layer 26. The heater layer 25 is connected to the thermo control circuit as well as the trowel-shaped far-infrared ray generator shown in FIGS. 1 and 2. Preferably, the heater layer 25 is constituted by one or two sheet-shaped silicon rubber heaters, which are provided in the tunnel. Especially, the suitable heater layer is a bendable sheet-shaped heater.

To use the dome shaped far-infrared ray generator, a patient lays face up on a mat 29 in a center part of the dome as shown in FIG. 6(2). A heater is accommodated in the mat 29 so as to warm the patient. Note that, the far-infrared ray genera or of the present invention may be provided on the upper side of the heater in the mat.

When electricity is applied to the heater layer 25 to generate heat, the far-infrared ray generating layer 26 is heated by the heat and irradiates far-infrared rays, so that the patient 23 laying in the center of the dome is intensively irradiated with the far-infrared rays as shown by arrows.

Since the heat-reflecting plate made of stainless steel is provided on the outer side of the heater layer 25, the far-infrared rays generated by the far-infrared ray generating layer 26 are reflected by the half-circular-shaped stainless steel and focused to the center part of the tunnel.

By using both domes D1 and D2, the entire body of the patient can be warmed; by using one of the domes D1 and D2, parts of the human body, e.g., main body part, lower abdomen, legs, can be selectively warmed. Therefore, the dome-shaped far-infrared ray generator is suitable for warming a relatively broad area of the human body.

After improving the circulation of blood by using the trowel-type far-infrared ray generator, metabolic decomposition products and harmful substances must be evacuated from the human body. Thus, the patient enters the dome-shaped far-infrared ray generator, which is capable of generating negative ions, so as to sweat a great deal. A characteristic of far-infrared ray is "reaching an inner part", namely a deep part of the human body can be warmed and the warmed state can be maintained for a long time so that high curative effects can be gained. In deep parts of the human body, the far-infrared rays are converted into thermal energy and warms the human body from the inside, so that blood vessels are expanded and blood circulation can be improved. Far-infrared rays activate molecular motion of water, so that flows of blood and biological fluids can be improved and cells can be activated. Further, much fresh oxygen can be supplied to cells, so that metabolism can be improved. By irradiating with far-infrared rays, glandula sebaceas are activated and stored sebum can be evacuated. Endocrine disrupters and heavy metals are also discharged from the human body together with the sebum. By the dome-shaped far-infrared ray generator, harmful sub stances can be discharged from glandula sebaceas together with sweat.

An minus ion mat may be piled on the warm mat 29, or the mat 29 may generate negative ions. By generating negative ions, the patient lying on the mat can absorb negative ions from a middle line of his back (medulla spinalis). The middle line is a nerve center, flow of internal electricity can be improved by absorbing negative ions from the nerve center. Negative ions make parasympathetic nerves of automatic nerves superior, so that pains can be relieved aid the patient can be relaxed. Further, negative ions remove active oxygen so that pains can be relieved and diseases, e.g., cancer, can be cured. Negative ions can be absorbed more from the middle line than mouth and nose.

In the vibration-type far-infrared ray generator shown in FIG. 5 and the dome-shaped far-infrared ray generator shown in FIG. 7, the far-infrared ray generating sections have the three-layered structures, but they may have the mixed structures, each of which includes two or three of tourmaline mineral, carbon and radon generating rare element mineral. Further, the carbon may work as the heating element.

The thermotherapy can be effectively performed by using the trowel-shaped far-infrared ray generator shown in FIGS. 1 and 2, the vibration-type far-infrared ray generator shown in FIG. 5 and the dome-shaped far-infrared ray generator shown in FIGS. 6 and 7 in order. In the present embodiment, the thermotherapy performed by using the trowel-shaped far-infrared ray generator shown in FIGS. 1 and 2 is called Step (1); the thermotherapy performed by using the dome-shaped far-infrared ray generator shown in FIGS. 6 and 7 is called Step (2); and the thermotherapy performed by using the vibration-type far-infrared ray generator shown in FIG. 5 is called Step (3).

In the step (1), the trowel-shaped far-infrared ray generating section of the far-infrared ray generator is pressed onto skin surface of a patient so as to irradiate the deep part of the patient; in the step (2), the patient enters and lies in the dome-shaped far-infrared ray generator so as to irradiate the entire body of the patient; and in the step (3), the hot towel including herb components is placed on the skin surface of the patient, and the vibration-type is pressed onto the hot towel so as to warm the patient with far-infrared rays.

Preferably, the step (1), which is capable of intensively and deeply irradiating a part of the human body, is first performed. In the step (2), far-infrared rays irradiate the entire human body in the dome, sweat comes out from the entire body as well as sauna, so that the body is wet; therefore, it is improper to perform the thermotherapy with the trowel-shaped far-infrared ray generator after the thermotherapy in the dome-shaped far-infrared ray generator. If the human body is wet, the trowel-shaped far-infrared ray generator cannot be easily moved, and the wet part is easily burnt.

By irradiating far-infrared rays in the dome, sweating and metabolism are promoted, so the entire human body becomes wet; thus, sweat is removed by placing the hot towel on the human body, applying vibrations and irradiating far-infrared rays. Since the herb components are included in the hot towel for relaxation, the step should be performed in the final stage of the three kinds of therapies.

The herb massage is performed for healing and relaxation. Parasympathetic nerves can be stimulated by the relaxation, so that an immunizing power can be improved. The thermotherapy is performed as "whole body treatment", "basic treatment" and "general treatment", and incurable diseases can be cured by the functions of negative ions, far-infrared rays and warming treatment.

In the step (1), the trowel-shaped far-infrared generator is capable of intensively warming the affected part so as to activate automatic nerves, smoothly flow lymph fluid and blood, promote metabolism of cells and evacuate metabolic decomposition products, so the trowel-shaped far-infrared generator is a highly effective apparatus. After the metabolic decomposition products and harmful substances are partially discharged from the body, then metabolic decomposition products and harmful substances are further discharged from the entire body with sweat in the step (2).

Further, in the step (3), efficacies of the herb or medical plant components are employed in the relaxation treatment. Namely, while massaging the human body in the step (3), the hot towel including the herb components is placed on and pressed onto the human body so that the herb components are absorbed in the human body in the step (3). The herbs or medical plants for the thermotherapy have been used for palliating pains and aromatherapy.

"Olfactory sense" of the five senses is close-knit with an emotion center of the brain, and biochemical and physical functions of aroma, which improve mental and physical conditions, have been verified. Herbal massage is effective for young men, old men, healthy men and sickly men to increase vitality and prevent and heal diseases.

In the step (3), the vibration-type far-infrared ray generator performs massage and thermotherapy with the hot towel, so the synergistic effects are very high. The unique feeling of happiness and the health effects, which are caused by the massage and the herb components, have been studied. The massage and the aromatherapy relax tensed muscles, so that, as described above, metabolic deco position products and harmful substances can be discharged, fresh oxygen can be supplied to blood, blood flow can be improved and the patient can recover.

Details of the far-infrared ray generator of the present invention will be further explained. The inventor has studied the heating elements 3, 20 and 25, the heat conductive metal plate 1, the adhesive for adhering the heating elements on the metal plate 1, the coat film on the metal plate, substances included in the coat film, etc. The inventor has invented the far-infrared ray generator for thermotherapy, which is capable of efficiently warm the human body.

The inventor has studied about the heating elements on the basis of sizes, shapes, electric capacity, heat resistance, etc., and found that preferable heaters were an aluminum case-type heater, a ceramic case-type heater, a silicon rubber heater, a sheathe heater and a mold press heater. For warming the human body as the thermotherapy apparatus, the proper ones were the ceramic case-type heater and silicon rubber heater.

In the far-infrared ray generator shown in FIGS. 1 and 2, the metal plate 1 is used so as to efficiently conduct heat from the heating element. The metal plate is made of aluminum or stainless steel and press-shaped to have the convex face, so that the metal plate has enough toughness and is capable of tightly contacting the human body. A coating film should be tightly adhered on the convex face; in case of the small metal plate, even if the metal plate is made of stainless steel having good coefficient of thermal expansion, the coating film is not peeled off from and the metal plate can be practically used. The metal plate made of aluminum can be practically used without any problems.

A glass plate may be used, instead of the metal plate, so as to smoothly slide. To tightly fit with the human body, the glass plate has an outer convex face. The glass plate may be made of soda glass, whose strength is equivalent to ordinary glass, preferably, reinforced glass or crystallized glass, which have great mechanical strength. In the case of using the glass plate, a coating material is applied on an inner concave face and dried or heat-treated.

A heating element is tightly attached on a rear face of the convex metal or glass plate (i.e., the inner concave face). To tightly fit, the heating element is fitted with, welded or adhered on the plate; thus, the inventor studied about heat conductivity, strength and workability, and found that the heating element could be suitably attached to the plate by an adhesive. The inventor compared heat conductivities and adhesive strength of several adhesives: thermosetting epoxy resin, silicone adhesive, phenol resin, so that they could be equally used as the adhesive.

By pressing the convex metal plate onto the human body for the thermotherapy, there is a risk of burn injury, thus the coating material should be applied on the outer convex face so as to relieve high heat conduction and prevent abrasion. The inventor compared organic coating materials with inorganic coating materials, and found that the inorganic coating materials had high abrasion-resisting property, high slidability, and were capable of effectively warming the human body as thermotherapy. On the other hand, the organic coating materials, e.g., organic thermosetting epoxy resin, whose abrasion-resisting property is slightly less than that of the inorganic coating materials, could be used as inexpensive coating materials. Glass components, which are the inorganic coating materials and whose softening point, are 680° C. or less, can be applied to the stainless steel plate; soda-lime lass components, whose softening points are 650° C. or less, and frit components, which have low softening points, can be applied to the aluminum plate. Both of the organic and inorganic coating materials can be applied to the glass plate, especially thermosetting adhesives are easy to use.

The inventor has studied "the effective far-infrared generating substances for thermotherapy", which are mixed with the inorganic coating material, for a long time and invented the present invention. The "effective far-infrared generating substances" are following three substances.

(1) Tourmaline mineral: it is a natural mineral and called electric stone, and its far-infrared ray effects are well known. (2) Dried and solidified substances including radium and radon components: they are collected from radioactive springs including radium and radon, and they have been known and used to cure rheumatism, gout, incised wound, etc. (3) Carbon: charcoal fire is capable of baking inner parts of foodstuffs, and far-infrared ray effects of wood charcoal have been well known. Particle diameters of the "far-infrared generating substances" (1), (2) and (3) mixed with the inorganic coating material are 0.125 mm pass of JIS standardized screen, preferably 0.074 mm pass. Only one of or at least two of the substances are mixed, then the mixture is kneaded with the inorganic coating material. Amount of each of the substances (1)-(3) is 1-30 weight part with respect to 100 weight part of the inorganic coating material, preferably 3-15 weight part. If the amount is less than 1 weight part, the far-infrared ray effects cannot be gained; if the amount is more than 30 weight part, the substances cannot be well kneaded so that the sufficient coating material cannot be produced.

0.5-2.0 wt % of binders, which include organic binders, e.g., CMC (synthetic binder), pulping waste liquid, and inorganic binders, e.g., clay, and water are mixed with the mixture, which includes the inorganic coating material and the "far-infrared generating substances", and they are well kneaded until having enough shape retaining property. The kneaded material is applied on the outer convex face of the metal plate with uniform thickness, then dried for a half day or more at room temperature, further slowly heated and dried at temperature of 40-110° C., and baked in an electric furnace at prescribed temperature: 680° C. or less for the stainless steel plate; 650° C. or less for the aluminum plate; and softening point or less for the glass plate.

Baking time is adjusted while observing the baking state. The "far-infrared generating substances" (1) and (2) may be changed by baking with the inorganic coating material at the temperature of 680° C. or less. Thus, samples of the substances (1) and (2), which had been heated for about 20 minutes at temperature of 680° C., were examined by an X-ray diffraction method, but no changes were observed.

When the substance (3) is baked, an inert gas should be introduced into the electric furnace so as to bake the substance in a deoxidizing atmosphere. The effective thermotherapeutic apparatus was firstly realized by combining: the heating element; the metal plate or the glass plate; the adhesive for adhering the heating element to the plate; the far-infrared ray generating substances; and the organic and inorganic coating materials. Further, an electronic thermo control unit, which is driven by a home electric source and which controls the temperature of the apparatus at 100° C. or less, was assembled, so that the new type thermotherapeutic apparatus capable of effectively warming the human body could be realized.

As described above, the far-infrared ray generator of the present invention, which is used for thermotherapy, includes the far-infrared ray generating member constituted by only one of or at least two of the tourmaline mineral, which efficiently irradiates far-infrared rays even at low temperature, the carbon and the solidified substances including radium and radon components, which are collected from radioactive springs. The far-infrared ray generating member is blended with the glass components, whose softening points are 680° C. or less, then the blended material is applied on the metal plate and baked. In another case, the far-infrared ray generating member may be blended with a commercially available heat-resisting organic resin, instead of the glass components, and the blended material may be adhered on the surface of the metal or glass plate. The blended material is heated by the heating element, whose temperature is adjusted to 100° C. or less.

The full course of the thermotherapy relating to the present invention is performed by the steps of: intensively irradiating far-infrared rays to an affected part of a patient by the trowel-shaped far-infrared ray generator; irradiating far-infrared rays to entire body of the patient, without insufficient irradiation, by the dome-shaped far-infrared ray generator shown in FIGS. 6 and 7 so as to evacuate toxins from the patient's body with sweat; placing a hot towel including herb components on the patient's body; pressing the vibration-type far-infrared ray generator onto the hot towel so as to warm and massage the patient's body.

Disease symptoms and curative effects of the full course of the thermotherapy will be explained with reference to several clinical cases.

Note that, each patient had the thermotherapy 2-3 times a week.

Case 1: adult woman, age 54; collagen disease; she had facial swelling and pains in entire body, and took many drugs. She had the thermotherapy for seven months, so that she has no facial swelling and pains now. Nothing abnormal was detected by blood examination.

Case 2: adult woman; age 39; she had a cancer operation in 2003 and took anticancer drugs four times; cancers spread to bone marrow and lympha, etc.; she had acute pains and used a wheel chair; she took morphine (for three months). She had the thermotherapy for one month, so that the pains were relieved, she stopped using morphine and the wheel chair. After three months, she had the thermotherapy three times a week. Nothing abnormal was detected by blood examination. She is doing fine now.

Case 3: adult woman; age 71; a disease of unknown cause; she had pains in entire body and could not walk. She had the thermotherapy for four months, so that she can walk now. Now, she has the thermotherapy once a week for prevention and enjoys travels.

Case 4: adult woman; age 64; intestinal blockage and uterine cancer spread to lungs; she had acraturesis after a radiation therapy. She had the thermotherapy for one year, so that the spread cancers disappeared, and the intestinal blockage was; improved. She is working now.

Case 5: adult woman; age 38; breast cancer spread to lympha; radiation therapy was recommended. She had the thermotherapy for seven months, so that the spread cancers disappeared. She is working as a house wife now.

Case 6: adult woman; age 66; lever cancer (estimated life expectancy was two months); she had abnormal cardiac rhythm and swelling of lower part of the body, and ascetic fluid stores in the body. She had the thermotherapy for eight months. Five years later, she is doing fine now.

Case 7: adult woman; age 72; bone cancer spread to lever with acute pains in back. She had the thermotherapy for seven months. Nothing abnormal was detected by pathological examination.

Case 8: adult man; age 73; nettle rash (having incurable patient card); he had irritated skin itches and pains in entire body. He had the thermotherapy for six months, so that the disease was completely cured. He is working now.

Case 9: adult woman; age 46; breast cancer; the breast cancer was removed but spread to other parts. She had the thermotherapy for six months. Nothing abnormal was detected by pathological examination. She is working now.

Case 10: adult woman; age 56; rheumatism with acute pains and deformation of joints; she had took large amounts of drugs. She had the thermotherapy for one year, so that the joints were improved without drugs. She is working now.

Case 11: boy; age 9; inoperable brain cancer. He had the thermotherapy for six months. He is doing fine and going to school now.

Case 12: boy; age 7; systematic atopic dermatitis; he had irritated skin in entire body, could not sleep due to itches, and took sleep-inducing drugs. He had the thermotherapy for two months, so that he was completely cured.

Case 13: girl; age 14; collagen disease; she had swelling and pains in entire body due to by-effects of drugs. She had the thermotherapy for seven months. GOT and GPT values were normal. She is going to school now.

Case 14: girl; age 14; hernia; she had acute pains in waste and was recommended to have surgery operation. She had the thermotherapy for two months. She recovered without operation, and she is doing fine and going to school now.

Case 15: boy: age 11: asthma; he had severe insults and needed oxygen inhalation. He had the thermotherapy for six months. He is doing fine now.

Case 16; adult woman; age 65; ademonia; she was hospitalized for seven years. She had the thermotherapy for six months, so that she stopped taking drugs. One year later, she could work. She is doing fine and working now.

Case 17: adult woman: age 45; automatic ataxia; she had taken sleep-inducing drugs and tranquilizing drugs for nine years. She had the thermotherapy for six months, so that she stopped taking drugs. She is doing fine and working now.

Case 18: adult woman; age 56; oervical spine hernia; she had taken headache drugs and tranquilizing drugs (for 20 years). She had the thermotherapy for one year, so that she stopped taking drugs and mental balance was restored. She is working now.

Case 19: adult man: age 32; Crohn's disease (incurable disease); he could not eat solid foods, so he had liquid foods and nutritional supplements. He had the thermotherapy for four months, so that the symptom was relieved. Seven months later, he could eat solidified foods. He is working now.

Case 20: adult woman: age 41; chronic ulcerative colitis (incurable disease); she had violent diarrhea and acute pains.

She had the thermotherapy for four months, so that she stopped taking drugs. The diarrhea was improved. Seven months later, she was recovered, and is now doing fine.

Case 21: adult man; age 62; leukemia; he had pains in entire body and could not walk. He had the thermotherapy for two months, so that he worked up his appetite. Eight months later, marker values were normal. One year later, he is doing fine.

INDUSTRIAL APPLICABILITY

As described above, the far-infrared ray generator of claim 1 comprises the far-infrared ray generating member used in the thermotherapy apparatus, which receives heat from the heating element and generates far-infrared rays, including only the radon generating rare element mineral, or at least two of the tourmaline mineral, the carbon and the radon generating rare element mineral, which are layered or mixed; when the far-infrared rays, which are generated by the far-infrared ray generating member, irradiate the human body, deep parts of the human body can be effectively warmed so that the far-infrared ray generator is useful for health and thermotherapy. By employing the far-infrared ray generating member to the trowel-shaped far-infrared ray generator, the vibration-type far-infrared ray generator and the dome-shaped far-infrared ray generator, a part of the human body can be intensively warmed. Further, the entire human body too can be effectively warmed, so that the far-infrared ray generators of the present invention are very useful for health and curing many diseases.

The invention claimed is:

1. A far-infrared ray generator for thermotherapy, comprising:
   a casing having a main part, which includes a glass plate having an outer convex face for contacting a human body and an inner concave face, and a handle part integrated with the main part;
   a far-infrared ray generating member being provided on the inner concave face of the glass plate, said far-infrared ray generating member including three far-infrared ray generating substances of a radon generating rare element mineral, tourmaline and carbon; and
   a heater for heating said far-infrared ray generating member, said heater being provided in said casing
   wherein said far-infrared ray generating member is formed by mixing radon generating rare element mineral powders, tourmaline powders and carbon powders with synthetic resin binders, and the mixture is baked and fixed on the inner concave face of the glass plate.

2. A far-infrared ray generator for thermotherapy, comprising:
   a casing having a main part, which includes a glass plate having an outer convex face for contacting a human body and an inner concave face, and a handle part integrated with the main part;
   a far-infrared ray generating member being provided on the inner concave face of the glass plate, said far-infrared ray generating member including three far-infrared ray generating substances of a radon generating rare element mineral, tourmaline and carbon; and
   a heater for heating said far-infrared ray generating member, said heater being provided in said casing
   wherein said far-infrared ray generating member includes a radon generating rare element mineral sheet, in which radon generating rare element mineral powders are solidified by synthetic resin, a tourmaline sheet, in which tourmaline powders are solidified by synthetic resin, and a carbon sheet, in which carbon powders are solidified by synthetic resin, and the sheets are layered on the inner concave face of the glass plate in that order by an adhesive.

3. A far-infrared ray generator for thermotherapy, comprising:
   a heater having a half-cylindrical shape and being capable of covering over a human body;
   a far-infrared ray generating member being provided on an inner face of said heater, said far-infrared ray generating member including a carbon layer, a tourmaline layer and a radon generating rare element mineral layer; and
   an outer protection layer formed on and covering over an outer face of said heater
   and further comprising an inner protection layer formed on and covering over an inner face of said far-infrared ray generating member.

* * * * *